United States Patent [19]

Yoon

[11] 4,085,743
[45] Apr. 25, 1978

[54] MULTIPLE OCCLUSION RING APPLICATOR AND METHOD

[76] Inventor: In Bae Yoon, 2213 Forest Ridge Rd., Timonium, Md. 21093

[21] Appl. No.: 663,103

[22] Filed: Mar. 2, 1976

[51] Int. Cl.² .................... A61B 1/06; A61B 17/12
[52] U.S. Cl. .................... 128/6; 128/303 A; 128/303.15; 128/326
[58] Field of Search .............. 128/303 A, 327, 326, 128/325, 6, 303.13, 303.1, 4, 2 B; 221/312 A, 238, 65, 298, 40, 36, 293; 206/339, 338, 340, 63.3, 805

[56] References Cited

U.S. PATENT DOCUMENTS

| 3,834,392 | 9/1974 | Lampman et al. | 128/303.13 |
| 3,870,048 | 3/1975 | Yoon | 128/326 |
| 3,911,923 | 10/1975 | Yoon | 129/303 A |
| 3,934,589 | 1/1976 | Zimmer | 128/303.1 |

Primary Examiner—Robert W. Michell
Assistant Examiner—Michael H. Thaler
Attorney, Agent, or Firm—Finnegan, Henderson, Farabow and Garrett

[57] ABSTRACT

A multiple occlusion ring applicator device and method for applying elastic occluding rings to an anatomical tubular structure which comprises an inner cylinder, an intermediate cylinder and an outer cylinder, said cylinders being slidably disposed with respect to each other, and forceps means slidably disposed within said inner cylinder, said inner cylinder, said intermediate cylinder, said outer cylinder and said forceps means cooperating to effect the application of multiple elastic occluding rings to the tubular structures without the necessity of removing the instrument from the patient's body for reloading purposes.

46 Claims, 17 Drawing Figures

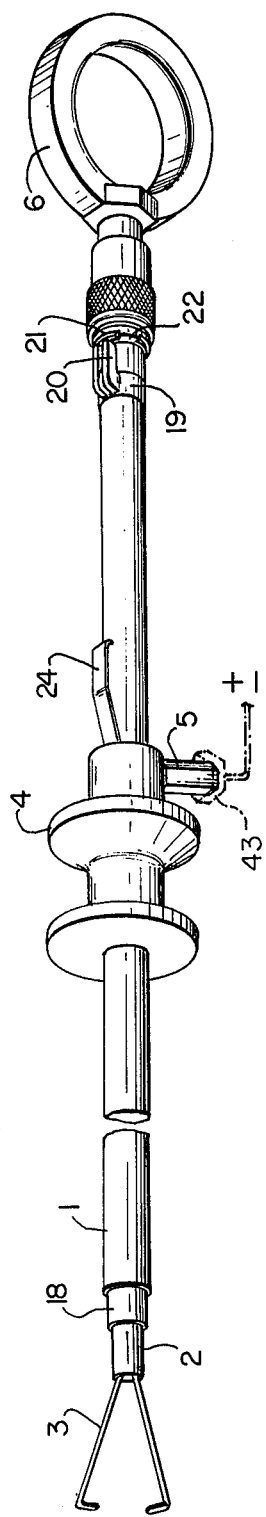
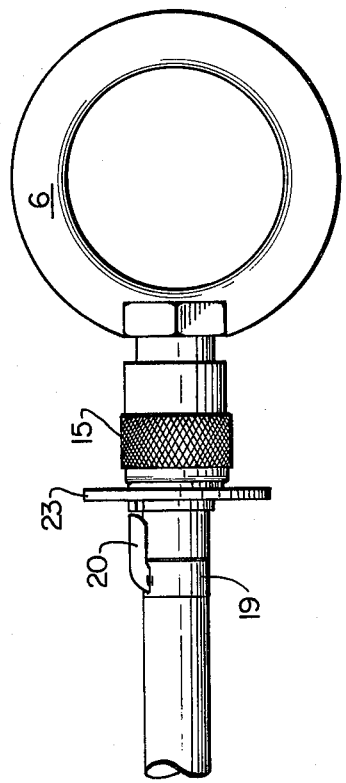
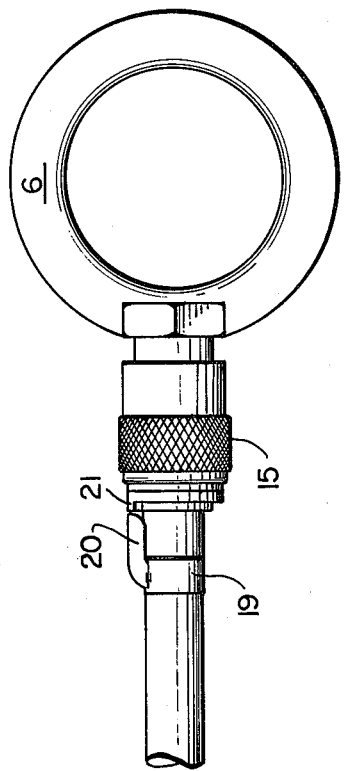

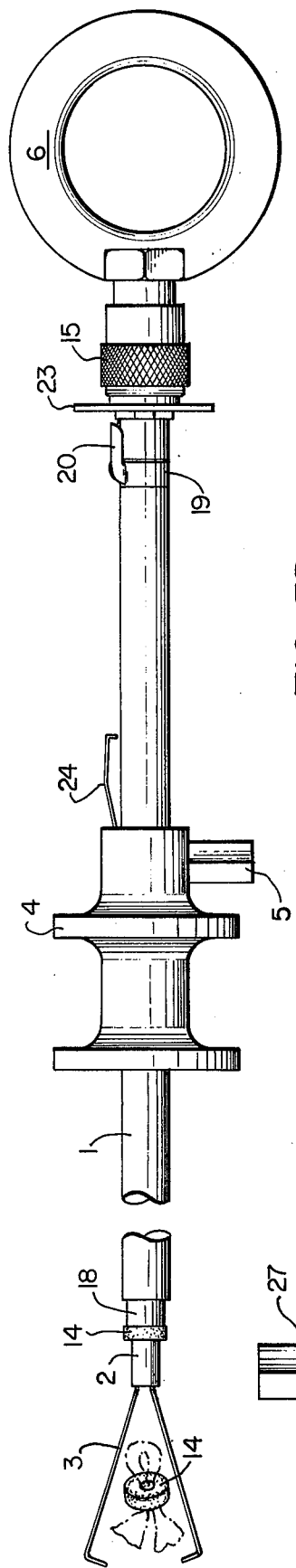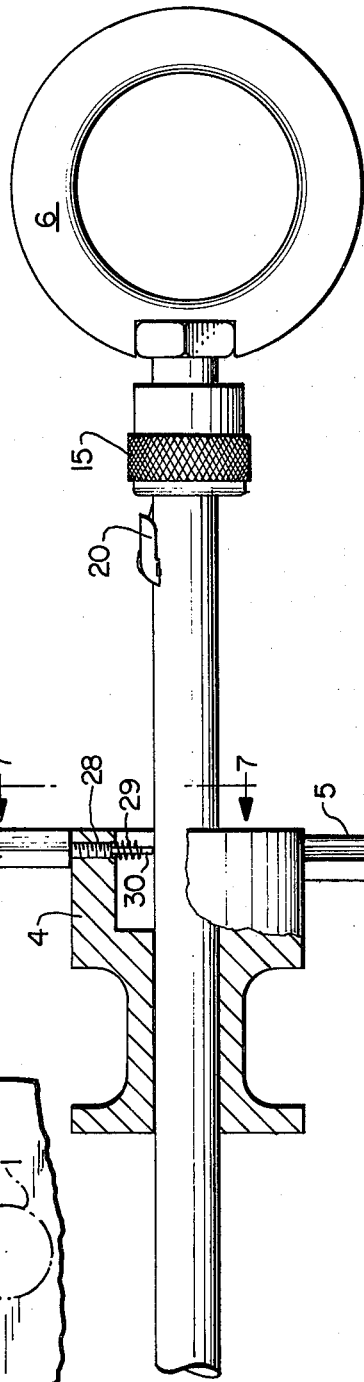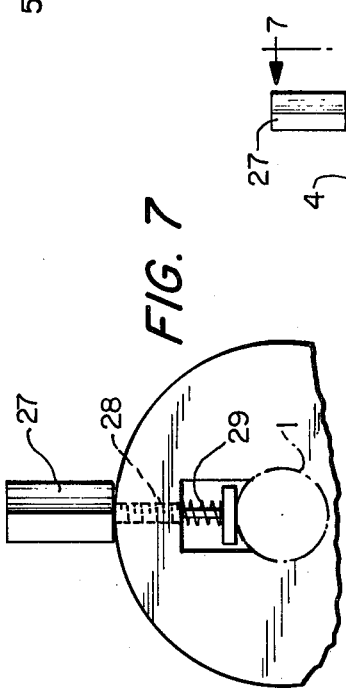
FIG. 5D
FIG. 6
FIG. 7

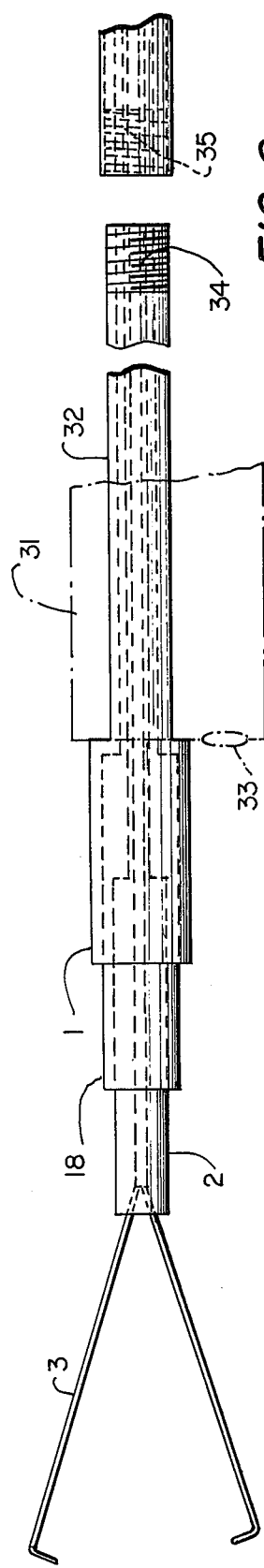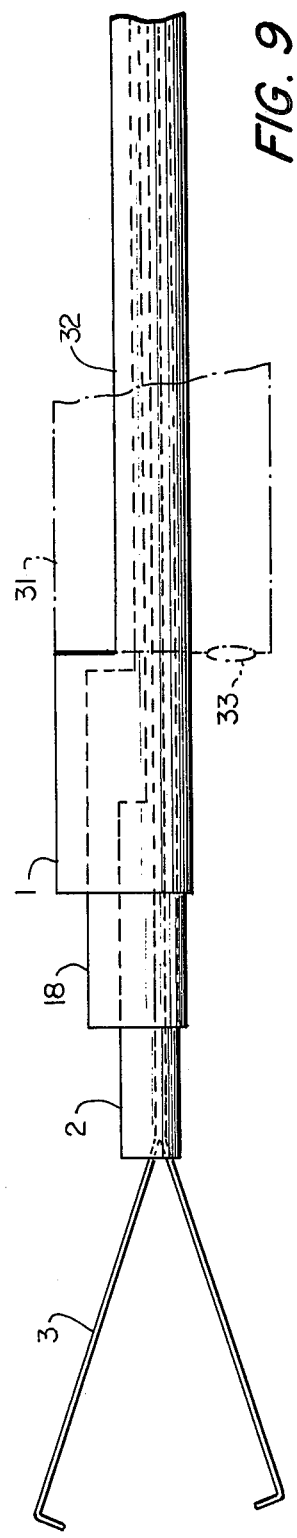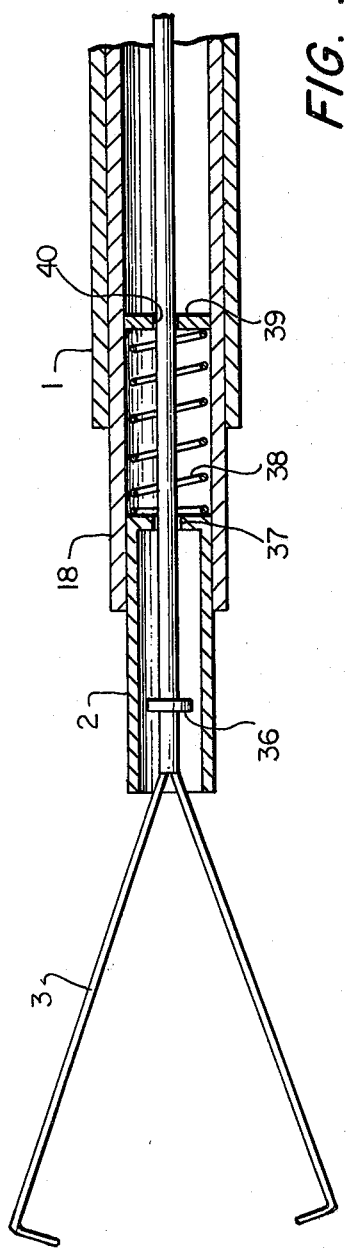

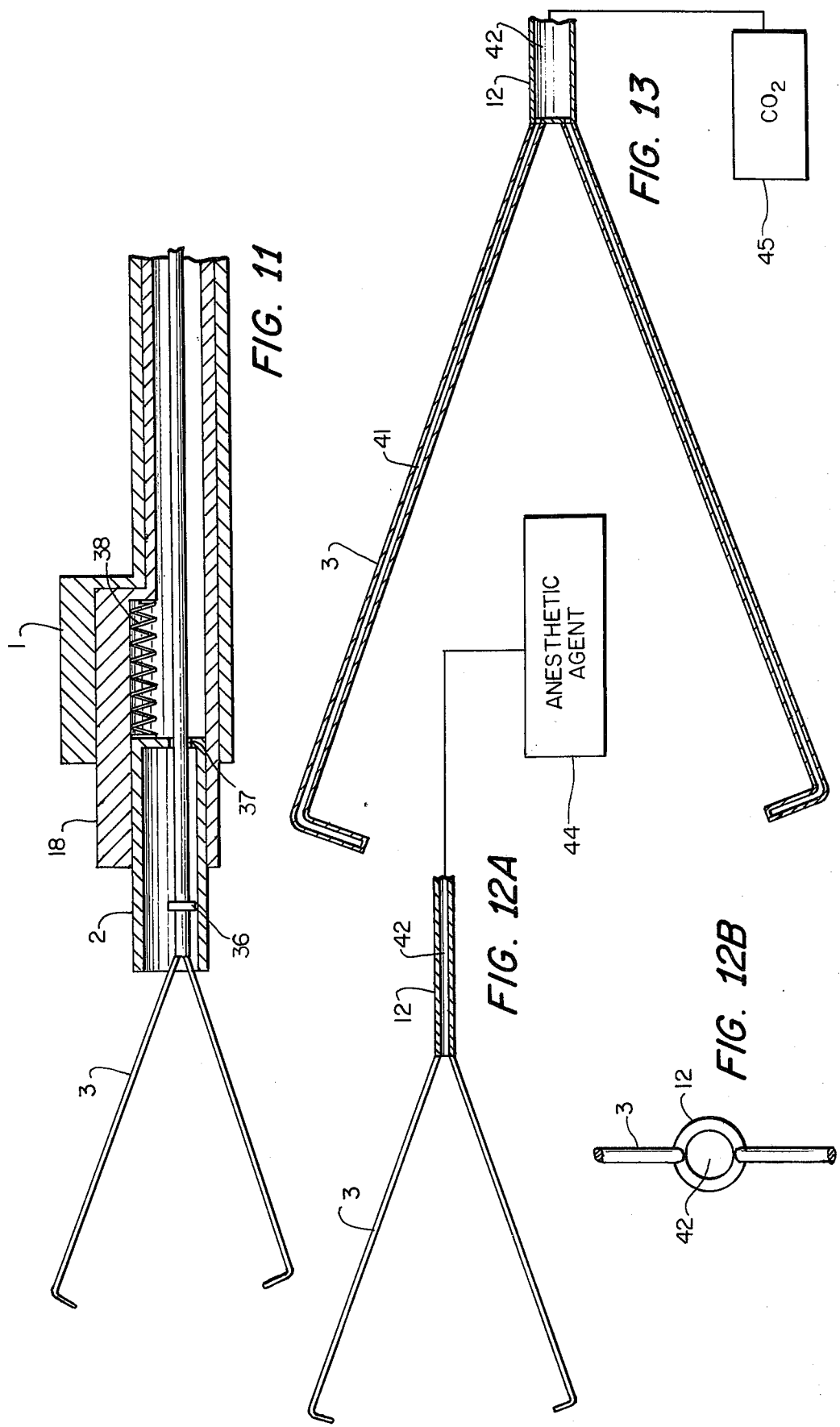

MULTIPLE OCCLUSION RING APPLICATOR AND METHOD

BACKGROUND OF THE INVENTION

The present invention relates to a multiple occlusion ring applicator device and method for applying a plurality of elastic occluding rings to anatomical tubular structures. More particularly, the present invention is directed to a ring applicator device which is effective in achieving the ligature of both of the Fallopian tubes of a female without the necessity of removing the instrument from the patient for the purpose of reloading the instrument. The device and method of the present invention is effective for carrying out the tubal ligation of the human female in order to effect temporary or permanent sterilization. The device and method of the present invention can also be utilized effectively to sterilize the human male.

In many areas of the world, the question of population control has become a central issue. Since birth control devices are not always used faithfully or fail to work in some instances, various procedures have been proposed for effecting the sterilization of women as well as men. However, many of these techniques are unpopular because of the resulting complications, the high expense, and because of the general unacceptability among the populace of effecting a sterilization which is permanent and cannot be reversed. Nevertheless, sterilization is obviously an effective means for solving various problems of population explosion and of voluntarily limiting the size of the family, where desired, on the part of the parent. Accordingly, research into finding various techniques and instruments has continued both under private and government support.

Tubal ligation has commonly been used to effect sterilization in women. The common practice is to cut and tie the Fallopian tubes in order to prevent fertilization of the egg. More recently, the use of clips for closing the tubes has been suggested. Another recent procedure involves cauterization of the tubes by electrical means. However, each of these procedures involves much discomfort to the patient, and highly skilled personnel are required to complete the operation successfully. Also, in the procedure requiring the use of clips, in some instances the clips have fallen off, thereby rendering the sterilization ineffective. With respect to cauterization by means of electricity, there remains the everpresent dangers of inadvertently burning certain organs of the body and, for example, accidentally rupturing the bowel.

In the recently developed ring applicator devices wherein the Fallopian tubes are ligated by an elastic ring, many of the above-mentioned difficulties have been eliminated. However, most of said ring applicator devices are capable of ligating only one Fallopian tube at a time. Thus, in such devices, after one of the Fallopian tubes has been occluded by placing an elastic ring around a knuckle formed in said Fallopian tube, it is then necessary to completely withdraw the instrument from the patient and reload the instrument with another elastic ring for ligating the second Fallopian tube. Such a technique is not only time-consuming, but also unduly complicates the tubal ligation procedure and, in some instances, can increase the ever possible chance of infection.

SUMMARY OF THE INVENTION

One of the objects of the present invention is to provide a simplified instrument and method for applying at least one occluding ring to an anatomical tubular structure.

Another object of the present invention is to provide a simplified instrument and method for effecting permanent or temporary sterilization of the human female.

A further object of the present invention is to provide a novel technique and instrument for accomplishing tubal ligation which may be employed by a physician with many degrees of skill and without the need of expensive or bulky equipment.

A still further object of the present invention is to provide a portable instrument for mechanically effecting tubal ligation wherein the grasping of the reproductive tubular member and effecting the release of one of the elastic rings around a knuckle (bend) formed in the tubular member to occlude it can be achieved through a single manipulation of a ring applicator device utilizing only one hand.

An additional further object of the present invention is to provide a multiple ring applicator device which is effective in ligating both of the Fallopian tubes of a female upon a single entry of the instrument into the body of the patient and without the necessity of removing the instrument from the body for reloading purposes.

A still further object of the present invention is to provide a ring applicator device which can be connected to a source of electrical current for performing certain electrical coagulation procedures.

Yet another object of the present invention is to provide an instrument which can also be used for the temporary or permanent sterilization of the human male.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

Pursuant to the present invention, the above-mentioned disadvantages may be eliminated and an improved ligature method and ring applicator device may be obtained by following the teachings of the present invention. In accordance with the present invention, the sterilization of the human male or the human female may be obtained by the use of elastic rings for effecting a ligature in the reproductive tubular member. Advantageously, the ligature is performed in conjunction with an endoscopic system, for example, a laparoscope, which is a device well known in the medical field for viewing the internal portions of the body.

The instrument of the present invention is a ring applicator which is used to quickly and effectively achieve the ligature of both of the Fallopian tubes of a female, in order to temporarily or permanently block the same, upon a single entry of the instrument into the body, and without the need of removing the instrument from the body for reloading purposes. The ring applicator device comprises a grasping means which is used to pull a portion of the Fallopian tube of the female into the device, thereby forming a knuckle or a bend in the Fallopian tube, and slidable cylinder means for slipping or pushing the elastic or stretchable ring over the portion of the Fallopian tube held in the device, thereby effecting the ligature.

The ring applicator device of the present invention comprises an inner cylinder, an outer cylinder and an intermediate cylinder coaxially disposed therebetween, said cylinders being slidably disposed with respect to each other. The proximal end portions of the three cylinders are so disposed with respect to each other that the inner cylinder extends beyond the intermediate cylinder and the intermediate cylinder extends beyond the outer cylinder. An elastic ring is mounted on the proximal end of both the inner and intermediate cylinders of the ring applicator device. A natural body entrance is then selected near the tubular member to be ligated. In the case of performing the sterilization of the human female, the natural body entrance would be either through the abdominal wall or through the vagina, depending upon the option of the physician. Since the ring applicator could also be used for shortening various ligaments by forming a knuckle therein, the natural body entrance would be selected near the particular tubular member which is desired to be shortened. In the next step of the method, entry is obtained through said natural body entrance by standard medical procedure. For example, when it is desired to ligate the Fallopian tubes, entrance through the abdominal wall may be obtained by making a small incision in the navel area. If the incision is made to be large enough, a light source may not be necessary. However, when a light source is utilized, then the two-hole technique is followed, that is, one incision is made for the ring applicator device and one incision is made for the light source. In the next step, a ring applicator is inserted through said entrance to the location area of said tubular member. Then, a grasping means which is slidably disposed within the inner cylinder, is pushed forward to engage a segment of the first Fallopian tube. The grasping means is then retracted into the inner cylinder of the ring applicator device a sufficient distance to form a knuckle or bend in the Fallopian tube and then the release of the elastic ring disposed on the inner cylinder is effected around the knuckle formed in the Fallopian tube, thereby occluding it. The grasping means can then be released to free the occluded portion of the Fallopian tube from the ring applicator device, leaving a ligatured Fallopian tube. In effecting the release of the elastic ring disposed on the inner cylinder, the inner cylinder is drawn axially into the intermediate cylinder, the end of the intermediate cylinder thus pushing the elastic ring from the inner cylinder to a position around the knuckle formed in the Fallopian tube. In sequence to the above procedure, the outer cylinder is caused to move axially with respect to the intermediate cylinder, thereby pushing the elastic ring disposed on the intermediate cylinder to the inner cylinder, thereby reloading the instrument in place so that it can be used to form a ligature in the second Fallopian tube. Thus, the grasping means is again pushed forward to engage a portion of the second Fallopian tube and then the grasping means is retracted into the inner cylinder of the ring applicator device and the second elastic ring is applied to the second Fallopian tube in the same manner as described above.

After the ring applicator device has been withdrawn from the body, the incision is closed through the use of standard medical procedure. If desired, the knuckles held by the elastic rings can be cut by the edges of the grasping means in order to effect permanent sterilization. Alternatively, the knuckles can be left as they are with the elastic rings holding the Fallopian tubes in a crimped position, thereby temporarily or permanently effecting sterilization. Temporary sterilization is contemplated by using an elastic ring which is sufficient to effect a ligature of the Fallopian tube, but is not so strong as to cut off the blood supply through the walls of the Fallopian tubes. When temporary sterilization is envisioned, the elastic rings can be removed from the Fallopian tubes in a subsequent operative procedure.

In the method and device of the present invention, the grasping of the reproductive tubular member by the ring applicator device with a second elastic ring is accomplished by a single manipulation of the ring applicator device using only one hand of the physician. Thus, after the tubular structure has been grasped by the grasping means, by withdrawing the operating slide by the fore and middle fingers in the rearward direction of the device, not only is the tubular structure drawn into the inner cylinder of the ring applicator by the grasping means, but also through the continual rearward operation of the operating slide, the inner cylinder is drawn within the intermediate cylinder, whereby the intermediate cylinder pushes the elastic ring from the proximal end of the ring applicator device around the crimped Fallopian tube. Then, by merely releasing the pressure being applied to the operating slide in the distal direction, the outer cylinder is caused to move in the proximal direction relative to the intermediate cylinder, thereby relocating a second elastic ring from the intermediate cylinder to the inner cylinder which effectively reloads the device for the application of a second elastic ring to the second Fallopian tube.

One of the most advantageous features of the present invention is that the instrument can be used as a multiple ring applicator which can achieve the ligature of both of the Fallopian tubes upon a single entry of the instrument into the body without the need of reloading the device.

Another feature of the present invention comprises a means for selectively charging the grasping means with an electrical current. Thus, if desired, the grasping means can be used to electrically sever and cauterize the Fallopian tubes, repair lesions, or perform any other type of procedure which would require an electrical current. The grasping means can be further modified for dispensing an anesthetic solution and for performing cryogenic surgery.

BRIEF DESCRIPTION OF THE DRAWINGS

The present invention will become more fully understood from the detailed description given hereinbelow and the accompanying drawings which are given by way of illustration only, and thus are not limitative of the present invention, and wherein, FIG. 1 illustrates a perspective view of the two-ring applicator of the present invention;

FIG. 3 shows one embodiment of the distal end portion of the ring applicator device of the present invention;

FIG. 4 shows another embodiment of the distal end portion of the ring applicator device of the present invention;

FIGS. 5A to 5D show, in sequence, the operation of the multiple ring applicator device of the present invention;

FIG. 6 shows a further embodiment for causing the outer cylinder to move axially relative to the intermediate cylinder for reloading the device;

FIG. 7 shows a section taken along line 7—7 of FIG. 6;

FIG. 8 shows the ring applicator device of the present invention provided with a bilateral enlargement of its proximal end portion;

FIG. 9 shows the ring applicator device of the present invention provided with a unilateral enlargement of its proximal end portion;

FIG. 10 shows the ring applicator device of the present invention with a shortened inner cylinder and a relocation of the spring mechanism from the distal to the proximal end portion of the instrument;

FIG. 11 shows the embodiment of FIG. 10 used in a unilateral enlargement of the proximal end portion of the ring applicator device;

FIG. 12A shows a grasping forceps means provided with a hollow shaft for the dispensing of an anesthetic agent;

FIG. 12B shows an end view of FIG. 12A; and

FIG. 13 shows a hollow grasping forceps means which communicates with a hollow shaft for performing cryosurgery.

DETAILED DESCRIPTION OF THE DRAWINGS

Figure 2:
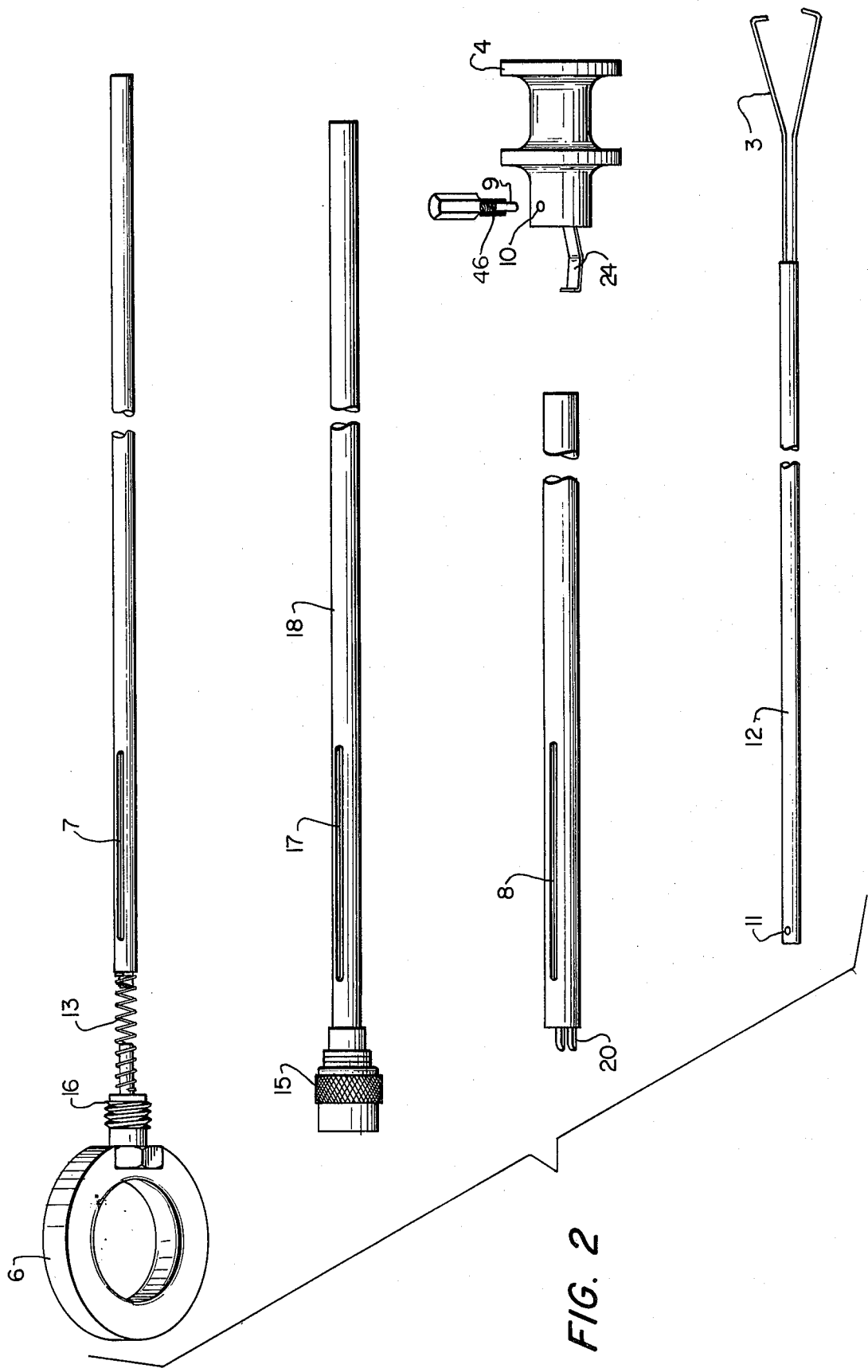
FIG. 2 shows the ring applicator device of FIG. 1 in a disassembled state.

In the following description of the figures, like numerals are used throughout the various views to indicate like elements. The device of the present invention comprises an inner tube or cylinder 2 disposed within an intermediate tube or cylinder 18 which, in turn, is disposed within an outer tube or cylinder 1, said inner cylinder being slidably engaged with said intermediate cylinder and said intermediate cylinder being slidably engaged with said outer cylinder. Thus, the inner cylinder 2, the intermediate cylinder 18, and the outer cylinder 1 can be axially moved relative to each other. The inner cylinder is further provided with grasping forceps 3 (grasping means), axially disposed therein. The grasping forceps springs open as they emerge from the inner cylinder. The outer cylinder is provided with an operating slide 4, which through the use of a locking screw 5, is placed in operative engagement with the outer cylinder, the intermediate cylinder, the inner cylinder, and the forceps tongs. The distal end of the ring applicator device is provided with a thumb ring 6 which is adapted to receive the thumb of the physician. The distal end of the outer cylinder is provided with an outer sleeve 19 which contains two spaced-apart, distally extending guide elements 20. The guide elements 20 are adapted to receive an inclined ridge 25 of an intermediate sleeve 26 which is disposed on the intermediate cylinder (see FIG. 5C). A collar 21 is rotatably disposed on the ring applicator device distal to the guide elements 20, said collar having cut-out groove portions 22. The operating slide 4 is provided with a spring rider 24. Thus, when the operating slide is pulled in the distal direction, the spring rider 24 rides up upon the guide elements 20 which abut against collar 21. Thus, as long as the collar 21 is in a position such that the grooved portion thereof 22 is not disposed behind the guide elements 20, the elastic ring reloading feature of the present invention will not come into play because the spring rider 24 will merely ride up upon the guide elements 20 and the collar 21 which forms a contiguous surface with said guide element. However, by rotating the collar so that the grooved portion is now disposed behind the guide elements 20, a small gap is produced immediately behind said guide elements. Thus, as the operating slide is pulled in the distal direction, the spring rider 24 rides up upon the guide elements 20 and falls within said gap and engages the distal end of said guide elements. Now, as the distal pressure produced on the operating slide is released, the spring mechanism of the device moves the operating slide in the proximal direction and the spring rider which is engaged with the guide element 20 pulls the outer cylinder in the proximal direction which reloads the ring applicator device by relocating the second elastic ring from the intermediate cylinder to the inner cylinder.

FIG. 3 shows the distal end of the ring applicator device of FIG. 1 in greater detail. It should be particularly noted that FIG. 3 shows the ring applicator device in a non-reloading position, that is, the guide elements 20 are in alignment with the non-grooved portion of the collar 21. In this position, the spring rider 24 will ride from the guide elements 20 to the collar 21 without any engagement taking place.

FIG. 4 is similar to FIG. 3 with the exception that the collar 21 is provided with a wheel 23 which facilitates rotating the collar 21 from the non-grooved to the grooved position.

FIG. 2 shows the ring applicator device of FIG. 1 in a disassembled state. The inner cylinder 2 is provided with a slot 7, the intermediate cylinder 18 is provided with a slot 17, and the outer cylinder 1 is provided with a slot 8, the slots 8 and 17 in the outer and intermediate cylinders being longer than the slot 7 in the inner cylinder. In its assembled state, the locking screw 5 which contains a stem 9 is screwed into a hole 10 provided in the operating slide 4, the stem 9 extending through the slot 8 in the outer cylinder, the slot 17 in the intermediate cylinder and the slot 7 in the inner cylinder and into the hole 11 provided in the shaft portion 12 of the forceps tongs 3. When the ring applicator device is assembled, the knurled nut 15 is in engaging relationship with the threaded portion 16 which is adjacent to the thumb ring 6.

Figure 5A:
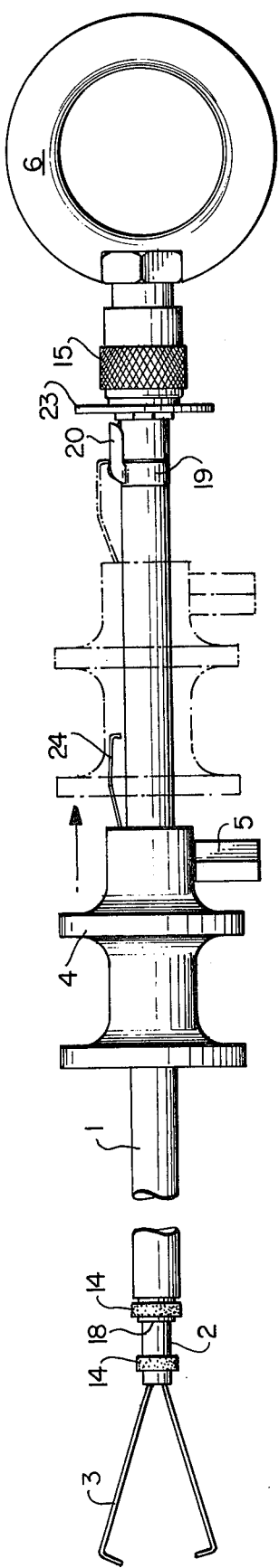
Figure 5B:
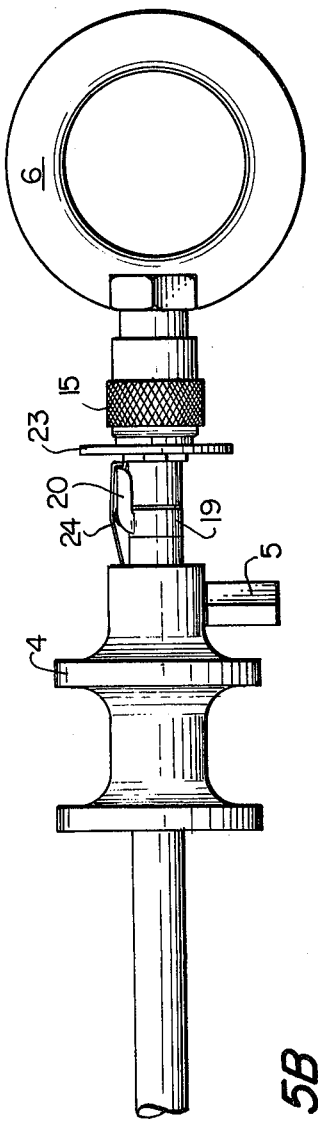
Figure 5C:
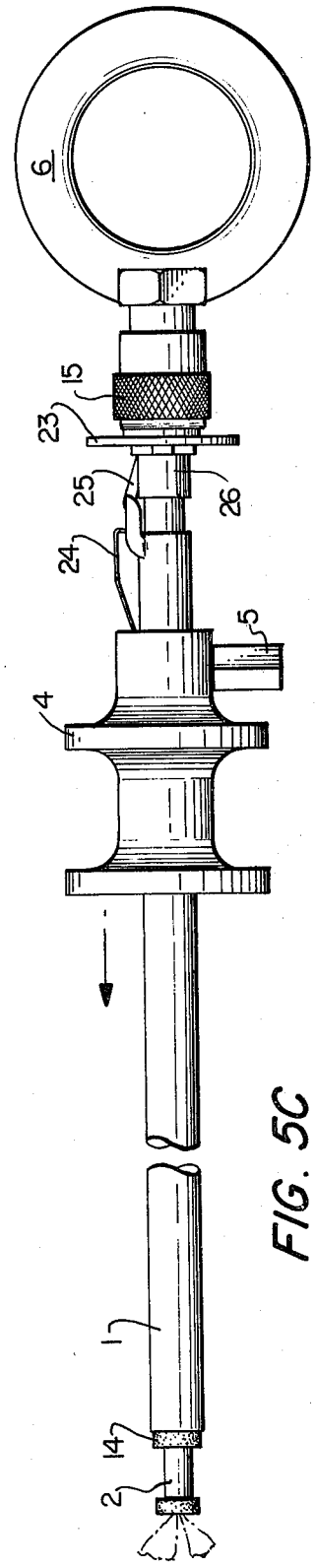

FIGS. 5A to 5D show the operation of the multiple ring applicator device of the present invention. FIG. 5A shows an elastic ring 14 mounted on both the inner and intermediate cylinders of the ring applicator device. When the operating slide 4 is moved from a position shown in FIG. 5A where the forceps tongs are extended from the proximal end of the ring applicator device toward the distal end of the ring applicator device, the stem 9 which is in an engaging relationship with the hole 11, pulls the forceps tongs containing a Fallopian tube into a position inside the proximal end of the inner cylinder of the ring applicator device. During this initial operation, since the stem of the locking screw slides through the slots 7, 17 and 8 of the inner, intermediate and outer cylinders, respectively, said cylinders do not move relative to each other. However, as the operating slide is continually moved toward the distal end of the ring applicator device, the stem 9 will eventually engage the end of the slot 7 of the inner cylinder and thus the inner cylinder will be moved in the rearward direction by the stem 9, thereby compressing the spring 13 and causing the inner cylinder 2 to move inside of the intermediate cylinder 18, which displaces the elastic ring 14 from the proximal end of the ring applicator device. The sliding of the operating slide in the rearward direction will be concluded when the stem 9 engages the end of the slots 17 and 8 in the intermediate and outer cylinders, respectively. Thus, the grasping of a reproductive tubular member and drawing it into a knuckle inside of the ring applicator device and the release of the elastic ring around said knuckle is effected through a single manipulation of the ring applicator device, that is, by merely sliding the operating slide with the fore and middle fingers to the rear of the ring applicator device. However, before the above operation takes place, the collar 21 is rotated so that the cutout grooved portion 22 is disposed immediately behind the guide elements 20. Thus, as the operating slide is drawn in its most distal position, which causes the inner cylinder to move inside of the intermediate cylinder, thereby displacing the elastic ring from the inner cylinder to a position around the crimped Fallopian tube, the spring rider 24 is placed into engaging relationship with the distal end portion of the guide elements 20 as shown in FIG. 5B. Then, by releasing the distal pressure being applied to the operating slide 4, the spring 13 automatically forces the operating slide 4 toward the proximal end of the ring applicator device. As the operating slide moves in this direction, the spring rider 24, which is fixed to the operating slide, and which is also in engaging relationship with the guide elements 20 pulls the outer cylinder in the proximal direction, relative to the intermediate cylinder, thereby displacing the elastic ring 14 from the intermediate cylinder to the inner cylinder, as shown in FIG. 5C, thereby reloading the instrument for a ligature of the second Fallopian tube. Thus, by merely drawing the operating slide in the distal direction, which compresses the spring 13 and then by merely releasing the distal pressure placed on the operating slide, the Fallopian tube is drawn into the inner cylinder, is ligated by the displacement of the elastic ring on the inner cylinder to a position around the crimped Fallopian tube, and the instrument is reloaded by displacing the second elastic ring from the intermediate cylinder to the inner cylinder. Then, the operating slide is moved in the proximal direction of the instrument, thereby extending the forceps tongs from the proximal end of the inner cylinder and releasing the Fallopian tube which has been occluded by the elastic ring 14, as shown in FIG. 5D. Now the ligature of the second Fallopian tube can be achieved by merely grasping a portion thereof with the forceps tongs 3 and drawing it inside of the inner cylinder and drawing the inner cylinder distally inside of the intermediate cylinder, thereby displacing the elastic ring 14 from the outside surface of the inner cylinder to a position around the crimped Fallopian tube. Then, by moving the operating slide in the proximal direction, the forceps tongs are extended beyond the proximal end of the inner cylinder, thereby releasing the second ligatured Fallopian tube. As can be seen by referring to FIGS. 5B and 5C, the distance which the outer cylinder is moved in the proximal direction relative to the intermediate cylinder by the spring rider 24 is determined by the inclined ridge 25. Thus, as the outer cylinder is drawn in the proximal direction by the spring rider 24 with the guide elements 20 is eventually released as the surface of the inclined ridge 25 approaches the surface of the guide elements 20. In effect, the inclined ridge 25 pushes the distal end of the spring rider 24 from engaging relationship with the guide elements 20, but only after the movement of the outer cylinder in the proximal direction has pushed the second elastic ring from the intermediate cylinder to the inner cylinder, thereby reloading the device. FIG. 5D shows the ring applicator device of the present invention wherein the first Fallopian tube has already been ligated and the instrument has been reloaded in preparation for the ligation of the second Fallopian tube.

FIGS. 6 and 7 show another means for moving the outer cylinder in the proximal direction relative to the intermediate cylinder for reloading the ring applicator device. In the embodiments shown in FIG. 6, the operating slide 4 is provided with a channel 28 for receiving an engaging screw 27. The engaging screw is adapted to screw around a center post 30 which is provided with a spring element 29. Thus, as the engaging screw 27 is tightened, the spring 29 is compressed, thereby pressing the base portion of the center post 30 against the outer cylinder. Thus, as the operating slide is pulled in the distal direction, the base of the post rides up upon the guide elements 20, thereby compressing spring 29, pushes the base of the post 30 into a locking position behind the distal end portion of the guide elements 20, thereby locking it in position. The release of the post from this locked position is facilitated by the inclined ridge 25 in the same manner as the release of the spring rider 24.

FIG. 8 shows a bilateral enlargement of the proximal end portion of the ring applicator device of the present invention. One of the reasons for this particular design is to adapt the ring applicator device of the present invention for use with the universally used endoscopic system which contains a 3-mm operating channel. Thus, the ring applicator can be provided with a reduced diameter portion which slides into the 3-mm operating channel of the endoscope 31. The proximal end of the ring applicator has a bilaterally enlarged portion of a size suitable for effecting the ligature of the Fallopian tubes, and if desired, having a larger size of up to 7 or 8 mm for other surgical purposes. In order to introduce the ring applicator of the present invention into the operating channel 32 of the endoscope 31, it is necessary to provide the ring applicator in two parts, which can be placed into screw engagement with each other. Thus, after the proximal end part of the ring applicator is placed into the operating channel of the endoscope, it can be joined to the distal end portion of the ring applicator by providing the grasping forceps, the inner cylinder, the intermediate cylinder, and the outer cylinder with male and female screw portions 34 and 35, respectively.

FIG. 9 shows the ring applicator device of the present invention provided with a unilateral enlargement of its proximal end portion. The advantages of this embodiment over FIG. 8 is that it provides a better field of vision for the physician by positioning the entire enlarged portion away from the lens system 33.

FIG. 10 shows the proximal end portion of the ring applicator device of the present invention with a shortened inner cylinder 2 and a relocation of the spring mechanism 38 from the distal to the proximal end portion of the instrument. The end of the inner cylinder is provided with an aperture 37 for slidably receiving the shaft 12 of the grasping forceps 3. The intermediate cylinder 18 is provided with a baffle 39 against which the spring 38 is compressed. The baffle 39 is also provided with an aperture 40 for slidably receiving the shaft 12 of the grasping forceps 3. Thus, as the grasping forceps is pulled in the distal direction by the operating slide, the grasping forceps pulls a segment of the Fallopian tube into the inner cylinder and the collar 36 which is larger than the aperture 37 in the inner cylinder engages the inner cylinder and pulls it distally by compressing the spring 38. Slightly before the inner cylinder reaches its most distal position, the intermediate cylinder pushes an elastic ring disposed on the inner cylinder to a position around a knuckle formed in the Fallopian tube. The reloading of the instrument is identical with that described hereinabove.

FIG. 11 shows the embodiment of FIG. 10 applied to a unilateral enlarged proximal end portion of the ring applicator device.

FIG. 12A shows the shaft 12 of the grasping forceps 3 provided with a hollow channel 42. Thus, if it is desired to introduce an anesthetic agent from the end of the hollow channel 42 between the grasping forceps 3, it would be necessary to provide the locking screw 5 with a hollow channel extending through the stem 9 and communicating with the hollow channel 42. Thus, by introducing an anesthetic agent from source 44 to the channel in the locking screw, it can be directed through the stem 9 and through the channel 42 in the shaft 12 to the end of the shaft between the grasping forceps.

In still a further feature of the present invention, the grasping forceps are also provided with a channel 41 which communicates with the channel 42 of the shaft 12. This particular embodiment enables the physician to perform cryosurgical techniques wherein a low-temperature $CO_2$ gas can be introduced from source 45 into the grasping forceps through an attachment communicating with the locking screw, similarly as with the anesthetic agent. Thus, the grasping forceps can be used to surgically freeze desired portions of the anatomy.

As shown in FIG. 1, the metal locking screw 5 can also be provided with a metal cap 43 which is connected to a source of electrical current. Thus, by electrically charging the cap 43, electrical current is transmitted through the locking screw 5, the stem 9, the shaft 12, and finally the forceps tongs 3. In such an installation, it would be necessary to insulate the stem 9 as by insulation layer 46 (FIG. 2) where it passes through the operating slots 7, 17 and 8 so that the inner, intermediate and outer cylinders are completely insulated from the electrical charge. Alternatively, the inner and outer cylinders can be made of a non-conductive plastic material and thus the electrical current would only be transmitted to the metal shaft 12 and the metal forceps tongs 3. As previously stated, such as addition to the ring applicator device of the present invention substantially increases its flexibility in that once the physician has introduced the instrument into the patient, he could conduct other medical procedures which would require an electrical current without removing the instrument from the patient.

With respect to FIGS. 1 to 13, particularly FIGS. 8 to 13, it should be noted that said figures are diagrammatic in nature and thus the dimensions of the various elements are shown as merely illustrative of the various possible features of the present invention.

The sterilization operation utilizing the ring applicator device as defined by the present invention renders sterilization so simple that only about 5 to 10 minutes are required to perform the operation and, accordingly, an out-patient procedure may be employed where permitted. This is particularly important in developing countries where hospital facilities are not abundant and may not even be available.

A particular advantage of the present invention is that the blockage of the tubes can be made permanent or temporary, as desired. This particular feature of the invention depends upon the size and the elastic power of the rings employed. If the rings are very small and have a strong elastic power, they will so tightly grip the Fallopian tubes that the blood supply in this part of the tube will be completely blocked, thereby resulting in a sluffing off of the knuckle formed in the tube to effect a permanent sterilization. However, if the elastic bands are of a larger size and/or have a smaller elastic power, it is possible to effect a temporary or reversible sterilization since, although the elastic band will serve to prevent the ovum passage to the uterus, the holding power thereof will not be so strong as to shut off the blood supply through the walls of the Fallopian tubes. In this situation, the knuckle formed in the tubes will remain and will not sluff off. Accordingly, if the woman should desire to return to a normal situation at a later time, it would be possible for the Fallopian tubes to be restored to their natural function by merely removing the elastic rings. Hence, the results of permanent or temporary sterilization are dependent upon the size of the rings used and/or the elastic power thereof.

The rings used for application to the Fallopian tubes are made of government-approved, non-tissue reactive material which has a strong enough elastic power to perform the function described herein. Various rubbery materials may, or course, be used. The preferred material is silicone rubber, for example, the material commercially available under the name "Silastic". Collagen or any other absorbable or non-absorbable synthetic elastic material which is not harmful to human tissue may be employed, for example, latex rubber or Teflon (tetrafluoroethylene). As pointed out above, the size of the rings may also be varied wherein smaller rings are used for permanent tubal ligation, and larger rings are used in connection with effecting a temporary sterilization. Spring-like metal rings, preferably made of stainless steel, can also be used, as discussed above.

The device of the present invention can be made of medically-approved materials, including many different types of metals, preferably stainless steel, plastics and the like. It can also be made as disposable instrument, for example, from a synthetic resin such as polyethylene, polypropylene, polycarbonate, polystyrene, polyamide, polyacetate, or acrylic resin. In this embodiment, the wall of the ring applicator can itself act as an endoscope for transmitting the light from a light source to the internal cavity. This embodiment of the invention would be especially attractive where inexpensive instruments are a necessity. Moreover, the ring applicator device of the present invention has a wide range of applicability since it can be used in conjunction with the regular abdominal laparoscopic technique, as discussed above, or in connection with the known vaginal culdascopic procedure. In this latter procedure, the instrument of the present invention can be curved. The use of the device eliminates the need for large, bulky equipment which is normally used with the electrical procedures employed in the prior art as well as the complicated carbon dioxide supply systems used with other techniques. A very simple and relatively small carbon dioxide supply system can be used together with the instrument, or a squeeze bulb may be used to provide the necessary gas and to maintain the required gas pressure inside the abdominal cavity while the operation is being performed. The elimination of complicated electrical and gas supply systems makes it possible to save time in setting up for the procedure. In addition, as pointed out above, the operation may be carried out quite quickly, in less than 10 minutes.

It is understood that various specific mechanical embodiments may be employed to perform the various functions described herein. Basically, the invention comprises an instrument for puncturing and entering into the body cavity, grasping the Fallopian tubes, slipping an elastic ring thereover, and optionally cutting the tubes, if desired. The associated equipment represents technical modifications and adds to this basic idea, and a particularly preferred embodiment is the use of the ring applicator of the invention together with a laparoscope or a similar viewing instrument.

As can be readily recognized, any optical endoscopic system can be utilized, for example, laparoscopes, culdoscopes, and hysteroscopes, in conjunction with the ring applicator device of the present invention. Thus, in particular endoscope must be modified so that it can be physically combined with the ring applicator device of the present invention.

In an analogous manner, the method and device of the present invention may be used to effect the sterilization of the human male. In this case, the appropriate incision is made and one or more elastic rings are applied to the vas to effect the ligature thereof and block the passage of the sperm. The elastic or stretchable rings used in this connection must, of course, be small enough to ligate the small diameter of the vas.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A multiple ring applicator device for applying elastic occluding rings to reproductive tubular members which comprises an inner cylinder provided with a first operating slot, and intermediate cylinder provided with a second operating slot, and an outer cylinder provided with a third operating slot, said second and third operating slots being longer than said first operating slot, said inner cylinder being slidably disposed within said intermediate cylinder and said intermediate cylinder being slidably disposed within said outer cylinder, forceps means slidably disposed within said inner cylinder, said forceps means containing a shaft portion, an operating slide means disposed on said outer cylinder, said operating slide means provided with connecting means which extend from the operating slide, through said third, second and first operating slots disposed in the outer, intermediate and inner cylinders, respectively, and into engaging relationship with the shaft portion of the grasping forceps means, guide means attached to the distal end portion of the outer cylinder and an engaging element attached to the operating slide, said engaging element being adapted to engage said guide means by moving the operating slide in the distal direction.

2. The multiple ring applicator device of claim 1, wherein when the operating slide means is in its forward, extended position, the grasping forceps extends from the inner cylinder, the proximal end portion of the inner cylinder extends beyond the proximal end portion of the intermediate cylinder, and the proximal end portion of the intermediate cylinder extends beyond the proximal end portion of the outer cylinder.

3. The multiple ring applicator device of claim 1, wherein the front end of the first, second and third operating slots are in alignment so that as the operating slide means is drawn toward the distal end of the device, the grasping forceps means is drawn into the inner cylinder and the connecting means engages the engaging surface of the rear end portion of the first operating slot which moves the inner cylinder in the distal direction relative to the intermediate and outer cylinders.

4. The multiple ring applicator device of claim 1, wherein the shaft of the grasping forceps is provided with an aperture and the connecting means is a locking screw which extends from the operating slide means through the first, second and third operating slots and into screw engagement with said aperture.

5. The multiple ring applicator device of claim 1, wherein a collar is rotatably disposed on the intermediate cylinder, distal to the guide means, said collar being provided with groove portions whereby, upon the rotation of said collar either a groove or a contiguous surface can be selectively provided behind the guide means.

6. The multiple ring applicator device of claim 5, wherein an inclined ridge is attached to the distal end portion of the intermediate cylinder and the guide means comprises two spaced-apart, distally extending guide elements which receive the inclined ridge of the intermediate sleeve, said inclined ridge releasing the engaging element from engaging relationship with the guide means as a result of the movement of the outer cylinder in the proximal direction.

7. The multiple ring applicator device of claim 5, wherein the collar has an enlarged diameter relative to the outer cylinder, thereby facilitating the rotation thereof.

8. The multiple ring applicator device of claim 5, wherein the engaging element is a spring rider.

9. The ring applicator of claim 5, wherein the engaging element is a spring-loaded element which is in pressure-engaging and sliding-engaging relationship with the outer cylinder.

10. The multiple ring applicator device of claim 1, wherein an optical viewing means and an illuminating means are combined with the ring applicator device.

11. The multiple ring applicator device of claim 10, wherein the optical viewing and illuminating means is an endoscope.

12. The multiple ring applicator device of claim 11, wherein the endoscope is a culdoscope.

13. The multiple ring applicator device of claim 11, wherein the endoscope is a hysteroscope.

14. The multiple ring applicator device of claim 11, wherein the endoscope is a laparoscope.

15. The multiple ring applicator device of claim 1, wherein means are provided for connecting a source of electricity to the forceps means.

16. The multiple ring applicator device of claim 1, wherein means which provide a source of electrical current is attached to the connecting means and insulating means are associated with the outer, intermediate and inner cylinders for electrically insulating said connecting means from said cylinders.

17. The multiple ring applicator device of claim 1, wherein the diameter of the inner, intermediate and outer cylinders are bilaterally enlarged at the proximal end portion of the device relative to the remaining portion of the ring applicator device.

18. The ring applicator device of claim 17, disposed in the operating channel of an endoscope such that the bilaterally enlarged portions of the ring applicator device extend beyond the front end portion of the endoscope.

19. The multiple ring applicator device of claim 1, wherein the diameter of the inner, intermediate and outer cylinders are unilaterally enlarged at the proximal end portion of the device relative to the remaining portion of the ring applicator device.

20. The ring applicator device of claim 19, disposed in the operating channel of an endoscope, said unilaterally enlarged end portion of the ring applicator device extending from the front end portion of the endoscope.

21. The multiple ring applicator device of claim 1, wherein the inner cylinder has a substantially shortened length relative to the intermediate and outer cylinders, and a spring means is disposed behind said inner cylinder in the proximal end portion of the ring applicator device.

22. The multiple ring applicator device of claim 21, wherein the shaft of the grasping forceps is provided with a disk-like element which engages the rear end portion of the inner cylinder and compresses the spring associated therewith by the distal movement of the grasping forceps means relative to the inner cylinder.

23. The multiple ring applicator device of claim 1, wherein the connecting means is provided with a hollow channel and the grasping forceps means is provided with a hollow channel, the hollow channel of the connecting means communicating with the hollow channel of the grasping forceps means and an aperture is disposed at the end of the hollow channel in the shaft of the grasping forceps means and means are provided for introducing an anesthetic agent to the connecting means.

24. The ring applicator device of claim 1, wherein the connecting means is provided with a hollow channel and both the shaft and the grasping forceps means are provided with interconnecting hollow channels, and means are provided for introducing a cold gas into said interconnecting channels.

25. The multiple ring applicator device of claim 1, wherein a spring means is disposed behind the inner cylinder in the distal end portion of the ring applicator device.

26. A multiple ring applicator device for use in sequentially applying multiple elastic occluding rings to anatomical tubular structures which comprises a cylinder like element, the proximal end portion of said cylinder-like element being adapted to receive an elastic occluding ring, forceps means slidably associated with said cylinder-like element and operative to grasp an anatomical tubular structure and draw it inside said cylinder-like element to form a bend therein, a first ring pushing means, the proximal end portion thereof being adapted to receive an elastic occluding ring, said first ring pushing means being movably and operatively associated with said cylinder-like element for displacing an elastic occluding ring from said cylinder-like element to a position around said bend, thereby forming a closed loop in said anatomical tubular structure, a second ring-pushing means movably and operatively associated with said first ring pushing means for displacing an elastic occluding ring therefrom to a position on the proximal end portion of the cylinder-like element to reload the device and operating slide means being in selective engaging relationship with the forceps means, the cylinder-like element and the first and second ring pushing means for effecting relative movement therebetween, thereby forming said closed loop in the anatomical tubular structure, reloading its device and discharging the occluded anatomical tubular structure from the device.

27. The multiple ring applicator device of claim 26, wherein the first ring pushing means and the second ring pushing means are intermediate and outer cylinders, respectively, and the cylinder-like element is an inner cylinder, said cylinders being coaxially disposed with respect to each other.

28. The multiple ring applicator device of claim 27, wherein a spring means is disposed behind the inner cylinder in the distal end portion of the ring applicator device.

29. The multiple ring applicator of claim 27, wherein, in the operatively ready position, the proximal end portion of the inner cylinder extends beyond the proximal end portion of the intermediate cylinder and the proximal end portion of the intermediate cylinder extends beyond the proximal end portion of the outer cylinder.

30. The multiple ring applicator of claim 27, wherein the operating slide means is disposed on the outer cylinder and connecting means provide communication between the operating slide means and the grasping forceps means independent of the inner, intermediate and outer cylinders, said grasping forceps means thereby being capable of independent movement in both the proximal and distal directions relative to the inner, intermediate and outer cylinders.

31. The ring applicator of claim 30, wherein the inner cylinder is provided with an engaging surface for engaging the connecting means independent of the intermediate and outer cylinders, said inner cylinder thereby being capable of independent movement in the distal direction relative to the intermediate cylinder and the outer cylinder.

32. The multiple ring applicator device of claim 31, wherein the grasping forceps means contain a shaft portion and the inner, intermediate and outer cylinders are provided with first, second and third operating slots, respectively, said connecting means extending through said first, second, and third operating slots and into engaging relationship with said shaft portion.

33. The ring applicator device of claim 32, wherein the first operating slot is shorter than the second and third operating slots, respectively, and the engaging surface for engaging said connecting means is the distal end of the first operating slot.

34. The multiple ring applicator of claim 33, wherein a spring means is operatively associated with the inner cylinder, said spring means being compressed by the movement of the forceps means and the inner cylinder in the distal direction relative to the intermediate cylinder and the outer cylinder.

35. The multiple ring applicator device of claim 27, wherein the operating slide means is provided with an engaging element which engages the distal end portion of the outer cylinder when said operating slide is moved in the distal direction.

36. The multiple ring applicator device of claim 27, wherein the operating slide is provided with a groove for receiving the fore and middle fingers of the physician and the distal end of the device is provided with a thumb ring.

37. The multiple ring applicator device of claim 27, wherein an optical viewing means and illuminating means are operatively combined with the ring applicator device.

38. A method of applying multiple elastic occluding rings to reproductive tubular members to effect at least temporary sterilization using a ring applicator device containing an inner cylinder, an intermediate cylinder and an outer cylinder, said inner cylinder being slidably disposed within said intermediate cylinder and said intermediate cylinder being slidably disposed within said outer cylinder which comprises loading each of the inner and intermediate cylinders with an elastic ring, forming a knuckle in a first reproductive tubular member and applying an elastic ring from the inner cylinder around said knuckle and repositioning an elastic occluding ring from a position on the intermediate cylinder to a position on the inner cylinder by displacing said cylinders relative to each other.

39. The method of claim 38, wherein a knuckle is formed in a second reproductive tubular member and an elastic ring is applied from the inner cylinder around said knuckle by displacing said cylinders relative to each other.

40. The method of claim 39, wherein a knuckle is formed in the first and second reproductive tubular member by drawing a section of said first and second reproductive tubular members inside of the inner cylinder.

41. The method of claim 38, wherein the elastic ring is applied to the reproductive tubular member by displacing the inner cylinder relative to the intermediate cylinder, and the ring applicator device is reloaded, in position, without removing the instrument from the body by displacing the outer cylinder relative to the intermediate cylinder.

42. The method of claim 41, wherein the inner cylinder is moved in the distal direction relative to the intermediate cylinder to apply the elastic ring to the knuckle formed in the reproductive tubular member and the outer cylinder is moved in the proximal direction relative to the intermediate cylinder to reload the ring applicator device by repositioning the elastic ring from the intermediate cylinder to the inner cylinder.

43. The method of claim 38, wherein the reproductive tubular members are Fallopian tubes.

44. The method of claim 38, wherein the reproductive tubular member is the vas.

45. A method of occluding a plurality of reproductive tubular members to effect at least temporary sterilization utilizing a single insertion of an elastic ring applicator device into the abdominal cavity which comprises selecting a site in the wall of the abdominal cavity near said reproductive tubular members, surgically penetrating the wall of the abdominal cavity to provide entry therein, inserting the elastic ring applicator device containing at least two elastic rings through said entry to the location area of said reproductive tubular members, grasping one of said reproductive tubular members while viewing said area, withdrawing said reproductive tubular member sufficiently to form a bend therein, effecting release of a first elastic ring around said bend in the reproductive tubular member to hold said tubular member in a bent position, whereby said tubular member is occluded and simultaneously displacing a second ring on said ring applicator device from a back-up position to a loaded, ready position on said device, releasing said reproductive tubular member from the ring applicator device to free the bent portion and repeating the above procedure with said second elastic ring to occlude a second productive tubular member and withdrawing said ring applicator device from the abdominal cavity, thereby leaving two occluded reproductive tubular members.

46. The method of claim 45, wherein the reproductive tubular members are fallopian tubes.

* * * * *